United States Patent [19] [11] Patent Number: 4,868,175
Engle [45] Date of Patent: Sep. 19, 1989

[54] 4-BENZYL-1-(2H)-PHTHALAZINEONE DERIVATIVES HAVING AN AMINO ACID RADICAL

[75] Inventor: Jürgen Engle, Alzenau, Fed. Rep. of Germany

[73] Assignee: Asta Pharma Aktiengesellschaft, Frankfurt am Main, Fed. Rep. of Germany

[21] Appl. No.: 192,060

[22] Filed: May 9, 1988

[30] Foreign Application Priority Data

May 8, 1987 [DE] Fed. Rep. of Germany ....... 3715273

[51] Int. Cl.$^4$ ................. C07D 403/04; C07D 403/14; A61K 31/55; A61K 31/50
[52] U.S. Cl. .................................... 514/212; 540/599
[58] Field of Search ......................... 514/212; 540/599

[56] References Cited
U.S. PATENT DOCUMENTS 3,813,384  5/1974  Vogelsang et al. ................. 260/239
3,894,015  7/1975  Stachel, deceased et al. ..... 540/599
4,746,656  5/1988  Atwal ................................. 514/212

FOREIGN PATENT DOCUMENTS 0174464  7/1985  European Pat. Off. .
3634942  5/1987  Fed. Rep. of Germany .

OTHER PUBLICATIONS

CA: 63654; Basically Substituted Benzylpthalazone Derivatives, Vogelsang et al., 5/28/74.
CA: 126670b, Histamindytic Basically Substituted Benzylpthalazone Derivatives, Vogelsang, 7/27/72.

Primary Examiner—Mary C. Lee
Assistant Examiner—John A. H. Russell
Attorney, Agent, or Firm—Cushman, Darby & Cushman

[57] ABSTRACT

Anti-asthmatically acting compounds of formula

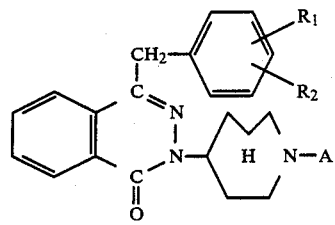

wherein $R_1$ and $R_2$ represent hydrogen, fluorine, chlorine, bromine, trifluoromethyl, $C_1$–$C_6$-alkyl or $C_1$–$C_6$-alkoxy and the radical A is the group

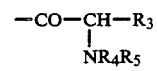

wherein $R_3$ is hydrogen, a phenyl radical, an indolyl-(3)-methyl radical, imidazolyl-(4)-methyl radical, a $C_1$–$C_{10}$-alkyl group or wherein $R_3$ represents a $C_1$–$C_{10}$-alkyl group which is substituted by a carboxy group, a $C_1$–$C_6$-alkoxycarbonyl group, an aminocarbonyl group, a hydroxy group, a $C_1$–$C_6$-alkoxy group, a $C_2$–$C_6$-alkanoyl-oxy group, a mercapto group, a $C_1$–$C_6$-alkylthio group, a $C_2$–$C_6$-alkanoylmercapto group, a phenyl group, a hydroxyphenyl group, a dihydroxyphenyl group, an amino-$C_1$–$C_6$-alkylthio group, an amino-$C_1$–$C_6$-alkyloxy group, an amino group, a ureido group ($H_2NCONH$—) or a guanidino group or wherein $R_3$ together with the structural moiety >CH(NHR$_4$) represents the pyrrolidine-2-yl-radical (proline radical) or the 4-hydroxypyrrolidine-2-yl radical, $R_4$ is hydrogen, benzyl or a $C_1$–$C_6$-alkyl radical, $R_5$ is hydrogen, benzyl, a $C_1$–$C_6$-alkyl radical, a $C_2$–$C_6$-alkanoyl radical or the group.

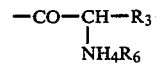

where $R_3$ and $R_4$ have the meanings given above and $R_6$ is hydrogen, benzyl or $C_2$–$C_6$-alkanoyl, and physiologically acceptable salts therof, and processes for their preparation.

3 Claims, No Drawings

4-BENZYL-1-(2H)-PHTHALAZINEONE DERIVATIVES HAVING AN AMINO ACID RADICAL

The present invention relates to new 4-benzyl-1-(2H)-phthalazinone derivatives having an amino acid radical which have an antihistaminic and antiallergic effects.

BACKGROUND OF THE INVENTION

Published German patent specification DAS No. 21 64 058 relates to basic substituted 4-benzyl-1-(2H)-phthalazinone derivatives having the following formula:

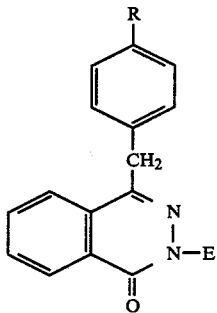

wherein R is a hydrogen or halogen atom, a trifluoromethyl group or a lower alkyl or alkoxy group and E is a 4-perhydroazepinyl, N-methyl-4-perhydroazepinyl, 3-quinuclidyl, 3-tropanyl, 3-nortropanyl, N-methyl-3-pyrrolidinyl or N-methyl-2-pyrrolidinyl methyl radical as well as physiologically acceptable acid addition salts hereof.

These compounds possess an antihistaminic effect.

SUMMARY OF THE INVENTION

The present invention relates to compounds of the formula

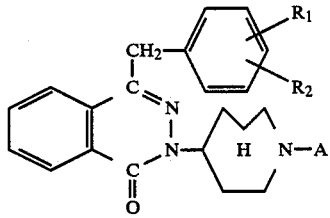

wherein $R_1$ and $R_2$ represent hydrogen, fluorine, chlorine, bromine, trifluoromethyl, $C_1$-$C_6$-alkyl or $C_1$-$C_6$-alkoxy and the radical A is the group

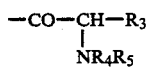

wherein $R_3$ is hydrogen, a phenyl radical, an indolyl-(3)-methyl radical, imidazolyl-(4)-methyl radical, a $C_1$-$C_{10}$-alkyl group or wherein $R_3$ represents a $C_1$-$C_{10}$-alkyl group which is substituted by a carboxy group, a $C_1$-$C_6$-alkoxycarbonyl group, an aminocarbonyl group, a hydroxy group, a $C_1$-$C_6$-alkoxy group, a $C_2$-$C_6$-alkanoyl-oxy group, a mercapto group, a $C_1$-$C_6$-alkylthio group, a $C_2$-$C_6$-alkanoylmercapto group, a phenyl group, a hydroxyphenyl group, a dihydroxyphenyl group, an amino-$C_1$-$C_6$-alkylthio group, an amino-$C_1$-$C_6$-alkyloxy group, an amino group, a ureido group ($H_2NCONH$—) or a guanidino group or wherein $R_3$ together with the structural moiety >CH(NHR$_4$) represents the pyrrolidine-2-yl-radical (proline radical) or the 4-hydroxypyrrolidine-2-yl radical, $R_4$ is hydrogen, benzyl or a $C_1$-$C_6$-alkyl radical, $R_5$ is hydrogen, benzyl, a $C_1$-$C_6$-alkyl radical, a $C_2$-$C_6$-alkanoyl radical or the group

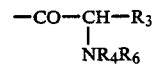

where $R_3$ and $R_4$ have the meanings given above and $R_6$ is hydrogen, benzyl or $C_2$-$C_6$-alkanoyl, and physiologically acceptable salts thereof.

The compounds of the invention of formula I are characterized by the following surprising effect: they have antiasthmatic, antiallergic, PAF-antagonist (PAF=platelet activating factor, a mediator that, inter alia, triggers asthma) as well as leucotriene inhibiting properties.

The following statements further describe preferred features of the present invention.

$R_2$ is preferably hydrogen.

The radical $R_1$ is preferably in the 4-position of the phenyl ring.

The alkyl groups, alkoxy groups, alkylamino groups, alkanoylamino groups, alkanoyloxy groups, alkanoylmercapto groups and/or the alkanoyl groups in general present in formula I may be straight or branched. The same also applies in the case of the alkyl or alkyloxy groups (=alkoxy groups) should these be components of other composed groups (for example in the form of a monoalkyl or dialkylamino group, alkanoylamino group, alkoxycarbonyl group, aminoalkylthio group, aminoalkyloxy group and analogous groups.)

The halogen atoms are, in particular chlorine and fluorine. The alkyl and alkoxy groups as such, or as components of other composed groups, consist in particular of 1–4 carbon atoms, preferably 1 or 2 carbon atoms. Alkanoyl groups, such as for example alkanoylamino groups, alkanoyloxy groups or alkanoyl mercapto groups consist in particular of 2–4, preferably 2–3 carbon atoms.

$R_3$ is for example a $C_1$-$C_6$-alkyl group which, in the 1-, 2-, 3-, 4-, 5- or 6-position (numbering always begins at the linkage of the alkyl radical with the rest of the molecule), has an amino group (in particular in the 3- or 4-position), a mercapto or hydroxy group (in particular in the 1 or 2 position), an amino-$C_2$-$C_4$-alkylthio group, an amino-$C_2$-$C_4$ alkoxy group, carboxy group, a $C_1$-$C_6$-alkoxycarbonyl group, a ureido group or a guanidino radical. For example, the group —CO—CH(NR$_4$R$_5$)—R$_3$ or —CO—CH(NR$_4$R$_6$)—R$_3$ is based on the following amino acids: asparaginic acid (DL form), asparagine, α-amino-butyric acid, leucine, isoleucine, ethyl asparaginate (L form), citrulline ($H_2N$—CO—NH—($CH_2$)$_3$—CH($NH_2$)CO$_2$—H, L form), ornithine (L form), arginine, 4-thialysine ($H_2N$—$CH_2$—CH$_2$—S—$CH_2$—CH($NH_2$)—COOH), 2,6-diaminooenanthic acid (δ-methyl lysine), 4-oxalysine ($H_2N$—$CH_2CH_2$—O—$CH_2$—CH($NH_2$)COOH), glycine, N-methylglycine, N,N-dimethylglycine, proline, hydroxyproline, alanine, β-alanine, 3,4-dihydroxyphenyl alanine, phenylalanine, tyrosine, tryptophan, cysteine, homocysteine (DL form), methionine, penicillamine, lysine (in particular L-lysine), valine, methyl valate (L form), threonine, histidine, serine, homoserine, glutamic acid, glutamine, α,β-diaminopropionic acid, sarcosine, ethionine, α,γ-diaminobutyric acid (L form), α-aminoadipic acid (L form).

The compounds of the present invention may be made by a process in which a compound of the general formula

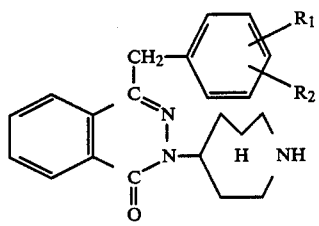

wherein $R_1$ and $R_2$ have the meanings given above is reacted with an acid of the general formula

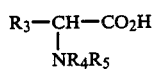

wherein $R_3$, $R_4$ and $R_5$ have the meanings given above, wherein the carboxy group can also be activated, where primary and second amino groups, carboxy groups, hydroxy groups and/or mercapto groups of the starting compound III present can be protected by conventional protective groups, splitting off any protective groups optionally present in the compounds obtained, alkylating or acylating optionally present free hydroxy groups, mercapto groups, primary or secondary amino groups and optionally converting the compounds obtained into their salts.

In accordance with the method of preparation, as noted above, hydroxy, mercapto and/or primary or secondary amino groups present in the products of the process may be alkylated or acylated. Alkylation may be carried out, for example, through reaction with compounds of formula MHal, $ArSO_2OM$ and $SO_2(OM)_2$, where Hal is a halogen atom (in particular chlorine, bromine or iodine) and Ar ia an aromatic radical (for example a phenyl or naphthyl radical optionally subatituted by one or more lower alkyl radicals) and M is a $C_1-C_6$-alkyl radical, a phenyl-$C_1-C_4$-alkyl radical, a halophenyl-$C_1-C_4$-alkyl radical or an amino-$C_1-C_6$-alkyl radical with a protected amino group. Examples are p-toluene sulphonic acid-$C_1-C_6$-alkyl esters, $C_1-C_6$-dialkyl sulphates, $C_1-C_6$-alkyl halides and the like. In the above-mentioned compounds the alkyl group may be straight or branched. The alkylation and acylation reaction is optionally conducted with the addition of conventional acid-binding agents, such as alkali hydroxides, alkali carbonates, alkali bicarbonates, alkaline earth metal carbonates, alkali acetates, tertiary amines (for example trialkylamines such as triethylamine), pyridine and also alkali hydrides at temperatures between 0° and 200° C., preferably 40° and 140° C. in inert solvents or suspension agents. Solvents or dispersing agents which may, for example, be used include: aromatic hydrocarbons such as, for example, benzene, toluene, xylene; aliphatic ketones such as, for example, acetone, methylethylketone; halogenated hydrocarbons such as, for example, chloroform, carbon tetrachloride, chlorobenzene, methylene chloride; aliphatic ethers such as, for example, butyl ether; cyclic ethers such as, for example, tetrahydrofuran, dioxane; sulphoxides such as, for example, dimethylsulphoxide; tertiary acid amides such as, for example, dimethylformamide, N-methylpyrrolidone, hexamethylphosphoric acid triamide; aliphatic alcohols such as methanol, ethanol, isopropanol, amylalcohol, tert.-butanol, cycloaliphatic hydrocarbons such as cyclohexane and the like. It is also possible to use aqueous mixtures of the solvents mentioned. The reaction is usually carried out at the reflux temperature of the solvents or dispersing agents used. The alkylation reaction components are frequently used in excess. The alkylation can also be carried out in the presence of tetraalkylammonium salts (in particular the halides) in combination with alkali hydroxides at temperatures between 0°-100° C., preferably 20°-80° C. in an aprotic solvent or in chloroform or methylene chloride. Aprotic solvents that may, in particular, be considered are: tertiary amides (dimethylformamide, N-methylpyrrolidone, hexamethylphosphoric acid triamide), dimethylsulphoxide, acetonitrile, dimethoxyethane, acetone, tetrahydrofuran.

Examples of acyl groups which may be introduced include $C_2-C_6$-alkanoyl groupa, a $C_1-C_6$-alkylcarbonyl groups, carbamoyl groups optionally substituted by one or two $C_1-C_6$-alkyl radicals or —CO—CH($NR_4R_6$)—$R_3$ groups. This process is conducted according to a manner known per se, preferably using the corresponding halide (for example carb-$C_1-C_6$-alkoxyhalides, $C_2-C_6$-alkanoylhalides), the corresponding anhydrides or also using the corresponding acids in the presence of known condensing agents [see for example process a)]. The reaction temperatures are, for example, between 30° and 120° C.

It is optionally possible to proceed in the following manner during alkylation and acylation in that there is first prepared an alkali compound (sodium, potassium or also lithium salt, for example) from the compound to be alkylated or acylated, by reacting it in an inert solvent such as dioxane, dimethylformamide, benzene or toluene with an alkaline, alkali metal hydride or alkali amide (in particular sodium or sodium compounds) or butyllithium at temperatures between 0° and 150° C. and then adding the alkylating agent.

Instead of the alkylating and acylating agents mentioned, it is also possible to use other chemically equivalent, conventionally used agents (see, for example, also L. F. and Mary Fieser "Reagents for Organic Synthesis", John Wiley and Sons Inc., New York, 1967, Vol. 1, pages 1303-4 and Vol. 2, page 471).

In the starting substances used for the process according to the invention, hydroxy groups, mercapto groups, carboxy groups, amino groups or $C_1-C_6$-alkylamino groups may be present which are protected by conventional protective groups.

These are conventional protective groups which may easily be split off by means of hydrolysis or hydrogenolysis and which are split off during or after the reaction. These are protective groups which are, for example, cited in the book by J. F. W. McOmie, "Protective Groups in Organic Chemistry", Plenum Press, New York, 1973, pages 43-143 as well as 183-215. Should such protective groups not be split off during the process reaction, splitting off takes place after the reaction. The starting compounds frequently contain such protective groups as a result of their preparation.

These protective groups can, for example, be readily solvolytically acyl groups or groups cleavable by hydrogenation. Solvolytically cleavable protective groups are, for example, split off by means of saponification with dilute acids (for example acetic acid, perchloric acid, hydrochloric acid, sulphuric acid, formic acid, trifluoroacetic acid) or by means of basic substances (potashes, soda, aqueous alkali solutions, alcoholic alkali solutions, $NH_3$) at temperatures between $-50°$ and $150°$ C., in particular between $0°$ and $100°$ C. Groups cleavable by hydrogenation such as arylalkyl radicals (benzyl radical) or aralkylcarbonyl radicals (carbobenzoxy radical) are conveniently split off using catalytic hydrogenation in the presence of conventional hydrogenation catalysts (precious metal catalysts), in particularly palladium catalysts or also platinum catalysts (platinum oxide) or Raney nickel in a solvent or suspension agent, optionally under elevated pressure (for example 1–50 bar) at temperatures between $20°–150°$ C., in particular $30°–100°$ C., preferably $40°–80°$ C. Solvents or suspension agents for the splitting off of such protective groups that may be considered are, for example: water, lower aliphatic alcohols, cyclic ethers such as dioxane or tetrahydrofuran, aliphatic ethers, halogenated hydrocarbons, dimethylformamide and the like, as well as mixtures of these agents. Protective groups which may be split off by means of hydrogenolysis that may, for example, be considered are: benzyl radicals, $\alpha$-phenylethyl radicals, benzyl radicals substituted in the aromatic ring (p-bromo or p-nitrobenzyl radicals), carbobenzoxyradicals or carbobenzthio radicals (whereby the aromatic ring may also be substituted in such radicals, for example by $NO_2$), tert.-butyloxycarbonyl radicals. Examples of radicals that may be split off hydrolytically are: phthalyl radicals, trityl radicals, p-toluenesulphonyl radicals, tert.-butyloxycarbonyl radicals, tert.-butyl radicals, dimethylmethylene radicals and other as well as lower alkanoyl radicals such as acetyl radicals, propionyl radicals, trifluoracetyl radicals, formyl radicals and the like.

Should the starting material contain free carboxy groups, it is often appropriate to esterify these first, for example using benzyl alcohol or another lower aliphatic alcohol (1–6, in particular 1–3 carbon atoms). In the final products such ester groups may, for example, be split off by means of bases, for example alcoholic alkali solution (for example methanolic KOH) or optionally also by means of mineral acids such as hydrochloric acid or sulphuric acid in alcoholic or aqueous alcoholic solution at temperatures between $20°$ and $100°$ C. or by means of hydrogenolysis.

It is in particular possible to use the protective groups conventionally used in peptide synthesis and the splitting processes conventionally used therein. Reference is made, inter alia, in this context to the book by Jesse P. Greenstein and Milton Winitz "Chemistry of Amino Acids"; New York, 1961, John Wiley and Sons Inc., Volume 2, for example page 883 et seq. The carbalkoxy group (for example of low molecular weight) is also suitable.

The compounds of the invention have a chiral center in the 7-membered ring as well as, in the majority of cases, additional asymmetric carbon atoms in the amino acid part A. The compounds of Formula I are therefore generally obtained as racemates or diastereomers. Such racemates may be resolved into the optically active isomers or enantiomers in a manner known per se, for example by fractional crystallization of the salts of racemic compounds I with optically active salts or optically active acids or also by means of chromatographic racemate separation (see, for example, "Angewandte Chemie" 92/1 [1980] page 14). It is, however, also possible to start with an optically active (starting) substance, so that a correspondingly optically active form is then obtained as final product. In the case of additional asymmetric carbon atoms diastereomeric mixtures are obtained. Separation may be effected using conventional methods.

The present invention thus includes the racemates and diastereomeric forms as well as the corresponding optically active leavo-and dextroratory forms.

Depending on the process conditions and starting substances the final substances of formula I are obtained in the free form or in the form of their salts. The salts of the final substances may be again converted into the bases in a manner known per se, for example with alkali, acids or ion exchangers. From the latter it is possible to obtain salts by reaction with organic or inorganic acids or with basic compounds, in particular those which are suitable for the formation of therapeutically usable salts.

Acids which are suitable for such salts include, for example, hydrohalic acids, sulphuric acid, phosphoric acids, nitric acid, perchloric acid, organic mono, di- or tricarboxylic acids of the aliphatic, alicyclic, aromatic or heterocyclic series as well as sulphonic acids. Examples thereof are: formic, acetic, propionic, succinic, glycolic, lactic, malic, tartaric, citric, ascorbic, maleic, fumaric, hydroxymaleic, gluconic or pyruvic acids: phenylacetic, benzoic, p-aminosalicylic acid, embonic acid, methanesulphonic, ethanesulphonic, hydroxyethanesulphonic, ethylenesulphonic acid; halobenzenesulphonic, toluenesulphonic, naphthalinesulphonic acid or sulphanilic acid or 8-chloro-theophylline.

The compounds of the invention are suitable for the preparation of pharmaceutical compositions. The pharmaceutical compositions or medicaments may contain one or more of the compounds of the invention. Conventional carriers and auxiliary materials may also be used in the preparation of pharmaceutical formulations.

The process may be carried out at temperatures between $0°$ and $150°$ C., preferably $40°$ and $100°$ C. in inert solvents or suspension agents. Solvents or dispersing agents which may, for example, be used include: aromatic hydrocarbons optionally substituted by chlorine or bromine, such as, for example benzene, toluene, xylene, chlorobenzene, pyridine; aliphatic ketones of low molecular weight (for example 3–6 carbon atoms) such as, for example, acetone, methylethyl ketone; halogenated hydrocarbons such as, for example, chloroform, carbon tetrachloride, chlorobenzene, methylene chloride; low molecular aliphatic ethers of low molecular weight (for example 4–10 carbon atoms) such as, for example, dimethoxyethane, butylether; saturated cyclic ethers such as, for example, tetrahydrofuran, dioxane; sulphoxides such as, for example, dimethylsulphoxide; tertiary acid amides such as, for example, dimethylformamide, tetramethylurea, N-methylpyrrolidine, hexamethylphosphoric acid triamide; acetonitrile; low molecular aliphatic alcohols such as methanol, ethanol, isopropanol, amylalcohol, tert.-butanol; cycloaliphatic hydrocarbons such as cyclohexane; low molecular saturated chloro- and fluorohydrocarbons with 1–5 carbon atoms, in which the individual carbon atoms may be two to three fold substituted by one or more chlorine and/or fluorine atoms, such as chloroform or methylene chloride. Aqueous mixtures of the solvents mentioned may also be used. The reaction is usually carried out at the reflux temperature of the solvents or dispersing agents used. It is optionally also possible to proceed in such a way that an alkali compound is first prepared of the compound II (sodium, potassium or also lithium salt, for example) by allowing it to react in an inert solvent such as dioxane, dimethylformamide, benzene or toluene with an alkali metal, alkali hydride or alkali amide (in particular sodium or sodium compounds) or butyllithium at temperatures between 0° and 150° C. and then reacting with compound III (for example in the form of the acid halide).

Should the free acid of formula III be used, this may be activated through the presence of condensing agents such as dicyclohexylcarbodiimide, sulphurous acid-bis-alkylamides (for example $SO[N(CH_3)_2]_2$), N,N'-carbonyldiimiazole and the like ("Organic Reactions", Vol. 12, 1962, pages 205 and 239).

Acids of formula III with an activated carboxyl group used in the process of the invention are preferably those of the general formula

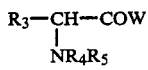

wherein $R_3$, $R_4$ and $R_5$ have the meanings given above and W is a halogen atom, a group of the formula —OR', —SR' or a group of the formula —OCO—R" and R' represents a $C_1$-$C_6$-alkyl radical or, if —OR' or —SR' is a phenyl radical, a phenyl radical substituted by nitro groups, $C_1$-$C_4$-alkoxy groups, $C_1$-$C_4$-alkyl groups or halogen atoms (chlorine, fluorine, bromine), a cyanomethyl radical or a carboxymethyl radical and R" is a straight or branched $C_1$-$C_6$-alkyl radical, a $C_1$-$C_6$-alkoxy radical, a phenoxy radical or a carbobenzoxy radical or the radical $R_3$—CH($NR_4R_5$)—.

If W represents a halogen atom this is preferably chlorine, bromine or iodine; should R' or R" represent alkyl radicals or alkoxy radicals these are preferably low molecular weight and have 1-4 carbon atoms.

Very often, particularly if W (formula IV) represents a halogen atom or the group —OCOR", acid binding substances such as alkali hydroxides, alkali carbonates alkali hydrogen carbonates, trialkylamines, dialkylamines, pyridine and the like or excess compound II may be present. In this case, the acid-binding agent may also be used on its own or in a mixture with other conventional solvents (for example pyridine). Care should be taken to ensure that unreacted starting substance III or IV, particularly if this is an acid chloride, is carefully neutralized and removed. It is frequently advisable to carry out chromatographic purification of the reaction product using silica gel, with, for example, elution with a chloroform-ethanol mixture (ethanol content for example 4%) optionally with the addition of aqueous ammonia.

Instead of the listed activation gents for the carboxyl group it is also possible to use other chemically equivalent agents conventionally used in chemistry. Such agents and processes are, for example, listed in the following literature references: L. F. and Mary Fieser "Reagents for Inorganic Synthesis", John Wiley and Sons Inc., New York, 1967, Vol. 1, pages 1303-4 and Vol. 2, page 471); Jakubke, Jeschkeit, "Amino acids, peptides, proteins", Akademie-Verlag, Berlin, 1982, 2nd Edition, pages 158-183. The previously cited references and their content according to the page numbers quoted are incorporated by reference herein.

Unknown starting compounds of formula II may be obtained by analogy with the disclosure of published German patent specification DAS No. 21 64 058 or German published patent specification DOS No. 35 30 793. The corresponding 2-phenacetyl-benzoic acids used as starting substances contain in the phenacetyl radical the radical $R_1$ and optionally $R_2$. In general one conveniently first produces the corresponding compound II, which contains a methyl group at the nitrogen of the 7-membered ring, and then this is cleaved via the carbethoxy compound by analogy with the examples in German published patent specification DOS No. 35 30 793. The initial compounds II with the methyl group on the nitrogen of the 7-membered ring may also be prepared according to, or analogous with, published German patent specification No. 21 64 058.

The compounds of the invention show a good antiasthmatic and antiallergic effect in the asthma test in conscious guinea-pigs. For example, an asthma-protective action against allergic asthma is observed in this test at a dose of 3 mg/kg bodyweight in guinea-pigs.

The lowest effective dose in the above-mentioned animal test is for example:

0.3 mg/kg oral 0.1 mg/kg intravenous

A general dosage range for this effect (in the above-described test) is for example:

0.1-30 mg/kg oral, preferably 1.0-10.0 mg/kg 0.1-10 mg/kg intravenous, preferably 0.3-5.0 mg/kg The direction of the action of the compounds according to the present invention is similar to the known medicine disodium cromoglicinic acid. However, the medicines of the present invention is distinguished in peroral effectiveness, greater effectiveness, longer-lasting effect.

Indications for which the compounds of the present invention can be employed are: allergic rhinitis, bronchial asthma.

Pharmaceutical preparations containing the compounds of the invention contain in general between 0.1 to 30, preferably 0.3 to 10 mg of the active ingredient.

The compounds according to the present invention can be administered in the form of tablets, capsules, pills, dragees (coated tablets), suppositories, ointments, jellies, creams, powders, dusting powder, aerosols or in liquid form. Possible liquid forms include aqueous solutions of administration include solutions in oils, alcohols and water as well suspensions and emulsions. A preferred dosage unit is a tablet which contains between 1 and 10 mg or solutions which contain between 1 and 10 weight percent of active ingredient.

The individual dosages of the active components are, for example, as follows:

(a) In the case of oral administration, between 0.1 and 30 mg, preferably between 1 and 10 mg.

(b) In the case of parenteral administration, for example intravenous, intramuscular, between 0.1 and 10 mg, preferably 0.3 and 5.0 mg.

(c) In the case of inhalation of the medicine, (solutions or aerosols) between 1 and 10 mg, preferably between 3 and 5 mg.

The dosages in each case refer to the amount of free base. In the case of salts, the dosage should be adjusted to provide the same amount of the base.

(d) In the case of dosage forms for rectal or vaginal administration, the dosage is between 0.5 and 50 mg, preferably between 1 and 30 mg.

(e) In the case of dosage forms for local administration to the skin and mucous membranes (for example in the form of solutions, lotions, emulsions, salves, etc.) between 1 and 10 mg, preferably between 3 and 5 mg.

For example, 1 to 2 tablets containing between 1.0 to 10 mg of active substance can be administered three times each day. Intravenous injections containing 0.3 to 5.0 mg of active substance can be administered once or twice each day. For oral administration, the minimum daily dose is 1 mg. The maximum daily dose for oral administration should not exceed 30 mg.

The individual oral dose for dogs and cats is generally in the range between about 0.5 and 30 mg/kg. The dose for parenteral administration is between about 0.1 and 10 mg/kg.

The individual oral dosage for treatment of horses and cattle is generaly between about 0.5 and 30 mg/kg; the parenteral dose is between about 0.1 and 10 mg/kg.

These dosages are in all cases the amount of free base.

The acute toxicity of the compounds according to the invention in the mouse (expressed as the LD 50 mg/kg; Method according to Miller and Tainter: Proc. Soc. Exper. Biol. a. Med. 57 (1944) 261) is for oral administration, in the range, for example, between 250 and 1000 mg/kg.

The medicines according to the invention can be used in human medicine, veterinary medicine and in agriculture, along or in combination with other pharmaceutically active substances.

The invention is illustrated by the following examples:

EXAMPLE 1

4-(p-Chloro-benzyl)-2-[hexahydro-1-glycyl-azepine-4-yl]-1-(2H)-phthalazinone

To a solution of 5.26 g (0.03 Mol) of N-tert.butyloxycarbonyl glycerine in 50 ml of dioxane are added with stirring 5g (0.03 Mol) of 1,1-carbonyldiimidazole at room temperature. After stirring for 60 minutes there is added dropwise at room temperature a solution of 11 g (0.03 Mol) of 4-(p-chloro-benzyl)-2-[hexahydroazepine-4-yl]-1-(2H)-phthalazinone (=demethylazelastine) dissolved in 80 ml of dioxane and the mixture is stirred for 4 hours at 40°-50° C. Thin layer chromatography shows that the reaction mixture still contains about 20% of unreacted demethylazelastine. 1.1 g of N-tert.-butyloxycarbonyl glycerine are therefore dissolved again in 20 ml of dioxane, reacted with 1 g of carbonyldiimidazole and added after 10 minutes with stirring to the reaction mixture. The reaction product is stirred for several hours (for example 2 hours) at 40° C. Thereafter the solvent is removed in a rotary evaporator, the residue is mixed with water and extracted 3 times with ether. The ether solution is then washed twice with water, dried with MgSO$_4$ and concentrated. The oily residue is dissolved in 50 ml of isopropanol and the solution is acidified with isopropanolic hydrochloric acid (5–10 ml) and heated for about 4 hours on a water bath (to cleave the butyloxycarbonyl protective group).

Then the solution cooled with ice, and the reaction product separates as an oil. The oily residue is mixed with diethyl ether, ground thoroughly and suctioned it is treated with isopropanolic hydrochloric acid, concentrated, treated with 50 ml of acetone and concentrated again using a rotary evaporator. The solid residue so obtained is then recrystallized from 25 ml of isopropanol and active charcoal, washed with ether and dried at 50° C. in a drying pistol.

Melting point of the hydrochloride: 187° C. Yield: 2.3 g.

The compounds set out in Table 1 are prepared by analogy with the preceding example. These are compounds of the general formula shown in Example 1.

Preparation and working up is effected by analogy with the procedure set out in Example 1.

In each case 0.03 Mol of the protected amino acid (for example N-tert.-butyloxycarbonyl-amino acid) is reacted with 0.025–0.03 Mol of 4-(p-chloro-benzyl)-2-hexahydroazepine-4-yl-1-(2H)-phthalazinone (=demethylazelastine) in a solvent (dichloromethane, dioxane). If the solvent be dichloromethane, the reaction takes place at reflux temperature. In this case, the reaction mixture is treated directly afterwards with water (for example 100 ml), the organic phase is separated, washed with water and the solvent removed.

The splitting off of the amino acid protective group is effected, for example, by heating with hydrochloric acid in isopropanol. Duration: 1–4 hours.

In Example 2 the product (hydrochloride) obtained after splitting off of the protective group is treated with water, extracted with diethylether to remove impurities, and subsequently the hydrochloric acid salt is extracted from the aqueous solution with dichloromethane. The residue obtained after removal of the dichloromethane is purified by brief heating with diisopropylether and then first by crystallization from isopropanol+charcoal and then from methanol+charcoal.

In Example 3 the amide product obtained after splitting off the protective group is dissolved in 50 ml of water, extracted twice the tert.-butylmethyl ether, the base is liberated in the aqueous solution with NH$_3$ and is extracted with dichloromethane. The isolated base is dissolved in 50 ml of acetone and converted to the hydrochloride with 2.8 ml of isopropanolic hydrochloric acid (5N HCl). The acetone is removed, the residue is dissolved in absolute ethanol, the ethanol is removed and the hydrochloride so obtained is heated to boiling with 100 ml of isopropyl ether and decanted from isopropyl ether and dried.

In Example 4 after splitting off the protective group the reaction solution contaiing isopropanol and aqueous hydrochloric acid is treated with 100 ml of diethyl ether and cooled to −20° C. The reaction product separates as an oil. After treatment with active charcoal in isopropanol and ethanol and removal of the solvent, the residue is treated with water, the base liberated with NH$_3$, and extracted with ether. After removal of the ether the base is diluted in 50 ml of acetone and the hydrochloride is prepared with 2.4 ml of hydrochloric isopropanol. The isopropanol is removed and the residue is heated to boiling in 100 ml of diisopropyl ether, and after cooling the hydrochloric acid salt is suctioned off and dried in vacuo at 60° C.

TABLE 1

| Example | R | Melting point of the HCl salt; °C. | Amino acid starting compound | Reaction medium | Yield |
|---|---|---|---|---|---|
| 2 | —CH₃ | 163 | BOC—L-Alanine | CH₂Cl₂ (110 ml in total) | 7.45 g |
| 3 | —CH(CH₃)₂ | 146 | BOC—L-Valine | CH₂Cl₂ (115 ml in total) | 5.7 g |
| 4 | —CH₂—C₆H₅ | 154 | BOC—L-Phenylalanine | CH₂Cl₂ (100 ml in total) | 5.4 g |

BOC = tert.-Butyloxycarbonyl

EXAMPLES FOR PHARMACEUTICAL FORMULATIONS

Tablets with 4 mg of compound according to Example 1.

40 g of active substance according to Example 1, 460 g of lactose, 150 g of corn starch and 10 g of aerosil are sieved (mesh size 0.8 mm), mixed and granulated with 200 g of a 5% aqueous gelatin solution in a fluidized bed. The dry granulate, 242 g of microcrystalline cellulose, 80 g of corn starch and 8 g of magnesium stearate are sieved (0.8 mm mesh size), homogenously mixed and pressed in the conventional way into tablets weighing 100 g and having a diameter of 6 mm.

1 tablet contains 4 g of active substance.

Capsules with 8 mg of compound according to Example 2

80 g of active substance according to Example 2, 50 g of corn starch, 1040 g of calcium hydrogen phosphate dihydrate and 10 g of highly pure silicon dioxide (aerosil) are passed through a sieve (0.8 mm mesh size), homogenized and granulated in a fluidized bed with 200 g of a 10% aqueous gelatin solution. 200 g of corn starch and the dry granulate are sieved (0.8 mm mesh size), homogenized and batched in the conventional manner into size 3 hard gelatin capsules each containing 140 mg. Each capsule contains 8 mg of active substance.

What is claimed is:

1. Compounds of the formula

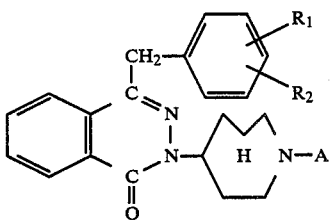

I wherein $R_1$ and $R_2$ represent hydrogen, fluorine, chlorine, bromine, trifluoromethyl, $C_1$–$C_6$-alkyl or $C_1$–$C_6$ alkoxy and the radical A is the group

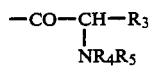

wherein $R_3$ is hydrogen, a phenyl radical, an indolyl-(3)-methyl radical, imidazolyl-(4)-methyl radical, a $C_1$–$C_{10}$-alkyl group or wherein $R_3$ represents a $C_1$–$C_{10}$ alkyl group which is substituted by a carboxy group, a $C_1$–$C_6$-alkoxycarbonyl group, an aminocarbonyl group, a hydroxy group, a $C_1$–$C_6$-alkoxy group, a $C_1$–$C_6$-alkanoyl-oxy group, a mercapto group, a $C_2$–$C_6$-alkylthio group, a $C_2$–$C_6$-alkanoylmercapto group, a phenyl group, a hydroxyphenyl group, a dihydroxyphenyl group, an amino-$C_1$–$C_6$-alkylthio group, an amino-$C_1$–$C_6$-alkoxy group, an amino group, a ureido group ($H_2$CONH—) or a guanidino group or wherein $R_3$ together with the structural moiety >CH(NHR₄) represents the pyrrolidine-2-yl radical (proline radical) or the 4-hydroxypyrrolidine-2-yl radical, $R_4$ is hydrogen, benzyl or a $C_1$–$C_6$ alkyl radical, $R_5$ is hydrogen, benzyl, a $C_1$–$C_6$ alkyl-radical, a $C_2$–$C_6$-alkanoyl radical or the group

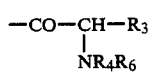

where $R_3$ and $R_4$ have the meanings given above and $R_6$ is hydrogen, benzyl or $C_2$–$C_6$-alkanoyl, or a physiologically acceptable salt thereof.

2. A pharmaceutical composition comprising an effective amount of a compound as set forth in claim 1 and a member of the group consisting of pharmaceutically acceptable carriers, diluents and auxiliary substances.

3. A method of treating asthmatic or allergic symptoms which comprising administering to a person exhibiting such symptoms an effective amount of a compound according to claim 1.

* * * * *